NECTARINE TREE
Filed Sept. 16, 1974
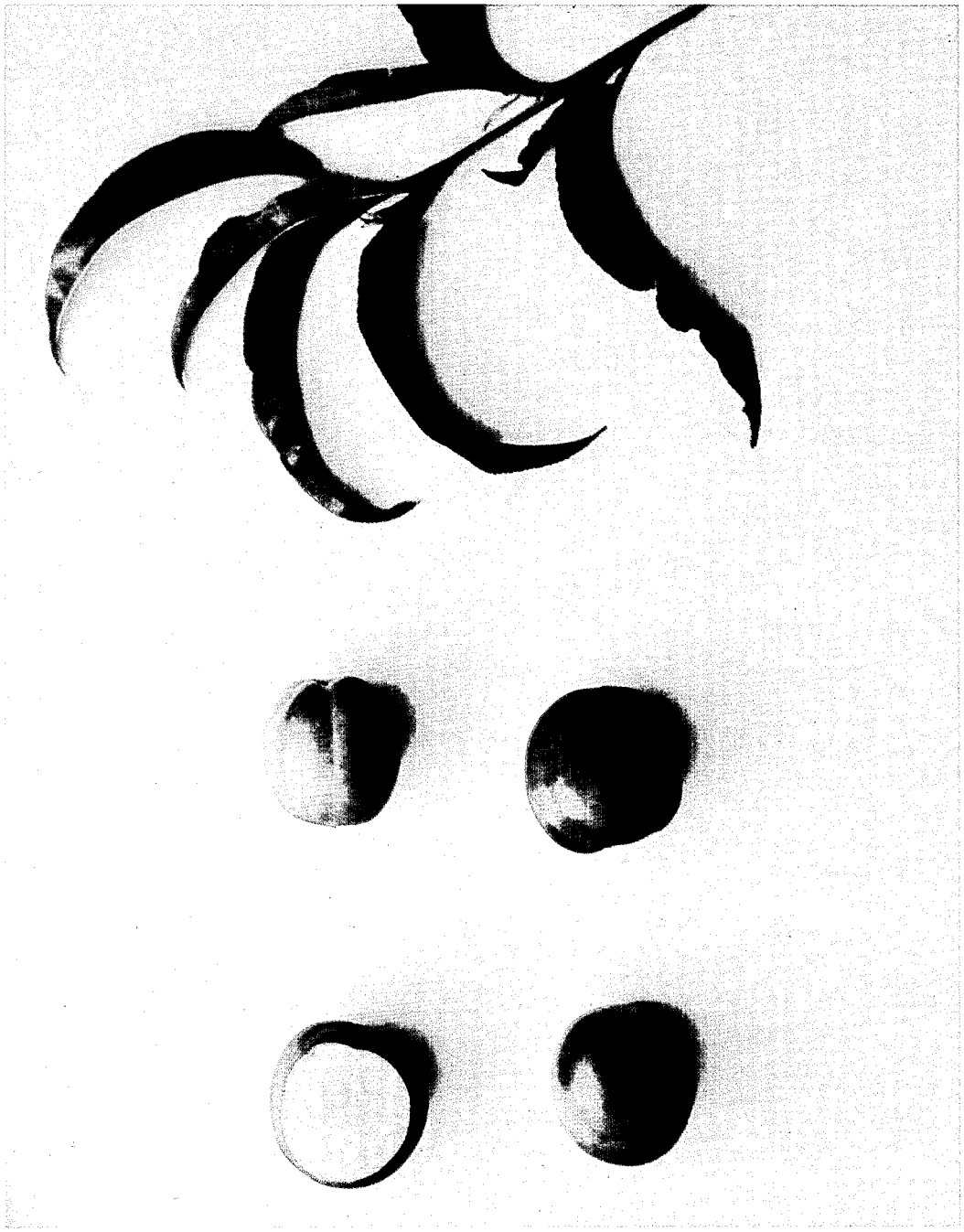

United States Patent

Plant Pat. 3,756
Patented Aug. 5, 1975

3,756
NECTARINE TREE

Frederic W. Anderson, Merced, Calif., assignor to Reedley Nursery, Inc., Reedley, Calif.

Filed Sept. 16, 1974, Ser. No. 506,751
Int. Cl. A01h 5/03
U.S. Cl. Plt.—41 1 Claim

ABSTRACT OF THE DISCLOSURE

A nectarine tree—classified in Group 118 of the classification established by Caillavet and Souty in their Monographie des Principales Varietes de Pechers, 1950 edition—which is large, vigorous, spreading, foliated with large-to-medium-size, lanceolate leaves having a crenate margin, and a regular and productive bearer of uniform, medium size, globose, semi-free-to-clingstone fruit having yellow skin substantially overspread with red, and yellow flesh; the fruit ripening about ten days earlier than the Red June nectarine (U.S. Plant Pat. No. 2,044).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me in my experimental nursery and orchard, located as aforesaid, as an open-pollinated seedling of the Red June nectarine (U.S. Plant Pat. No. 2,044). A large number of seeds of such parent variety were planted and the resultant seedlings grown under careful and continuing observation by me. One of such seedlings—and which is the present variety—evidenced novel and distinctive charteristics favorable for commercial growing, and I, therefore, selected such one seedling for asexual reproduction.

ASEXUAL REPRODUCTION OF THE VARIETY

I successfully asexually reproduced the present variety of nectarine tree by top-working on orchard trees in my said experimental orchard, and in maturity such reproductions were found to run true—in all respects—to the parent tree and its fruit.

SUMMARY OF THE VARIETY

The present variety of nectarine tree is large, vigorous, spreading, foliated with large-to-medium-size, lanceolate leaves having a crenate margin, and a regular and productive bearer of uniform, medium size, globose, semi-free-to-clingstone fruit having yellow skin substantially ovrespread with red, and yellow flesh; the variety, while generally resembling the Red June nectarine, being essentially distinctively characterized by fruit which ripens about one week earlier, is not quite as firm, and has more mottling on the surface of the skin.

BRIEF DESCRIPTION OF THE DRAWING

The drawing is an illustration, by photographic reproduction in color, of a twig with leaves, and separate fruit; one of the latter being cut to expose the flesh.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading
- *Production.*—Productive.
- *Bearing.*—Regular bearer.

Trunk:
- *Size.*—Medium.

Branches:
- *Size.*—Medium.

Leaves:
- *Size.*—Large to medium. Average length—6⅜". Average width—1⅜".
- *Form.*—Lanceolate.
- *Thickness.*—Medium.
- *Margin.*—Crenate.
- *Petiole.*—Medium length.
- *Glands.*—Average number—3. Reniform. Usually positioned 2 on blade and 1 or 2 on petiole.
- *Color.*—Top side—Medium green (22–L–9). Under side—Lighter green (21–K–7).

Flower buds:
- *Size.*—Medium.

Flowers:
- *Blooming period.*—About with Red June nectarine. Medium, as compared with other varieties.
- *Size.*—Large.
- *Color.*—Pink.

Fruit:
- *Maturity when described.*—Eating ripe—June 7, 1974.
- *Date of first picking.*—May 28, 1974.
- *Date of last picking.*—June 7, 1974.
- *Size.*—Uniform. Medium. Average diameter axially—2¼". Average transversely in suture plane—2¼".
- *Form.*—Globose.
- *Suture.*—Distinct. Extends from base to apex, with slight depression beyond pistil point.
- *Apex.*—Short.
- *Pistil point.*—Inconspicuous.

Skin:
- *Thickness.*—Medium.
- *Tendency to crack.*—None noted.
- *Down.*—Wanting.
- *Color.*—Yellow (9–L–4) overspread with red (5–L–6), shading to darker red (6–L–6). Many yellow flecks.

Flesh:
- *Texture.*—Medium. Meaty. Melting.
- *Ripens.*—Evenly.
- *Flavor.*—Sub-acid.
- *Eating quality.*—Good.
- *Color.*—Yellow (10–L–5).

Stone:
- *Type.*—Semi-free to cling.
- *Size.*—Medium. Average length—1½". Average breadth—⅞". Average thickness—¾".
- *Tendency to split.*—Slight.
- *Color.*—Beige (11–I–6).

Use: Market—local. Dessert.
Keeping quality: Medium.
Resistance to insects and diseases: No unusual susceptibilities noted.
Shipping quality: Medium.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, spreading, foliated with large-to-medium-size, lanceolate leaves having a crenate margin, and a regular and productive bearer of uniform, medium size, globose, semi-free-to-clingstone fruit having yellow skin substantially overspread with red, and yellow flesh; the variety, while generally resembling the Red June nectarine, being essentially distinctively characterized by fruit which ripens about one week earlier, is not quite as firm, and has more mottling on the surface of the skin.

No references cited.

ROBERT E. BAGWILL, Primary Examiner